US012594373B2

(12) United States Patent
Müller

(10) Patent No.: US 12,594,373 B2
(45) Date of Patent: Apr. 7, 2026

(54) PACKAGE ASSEMBLY

(71) Applicant: SHL MEDICAL AG, Zug (CH)

(72) Inventor: Stephan Müller, Hemishofen (CH)

(73) Assignee: SHL Medical AG, Zug (CH)

( * ) Notice: Subject to any disclaimer, the term of this patent is extended or adjusted under 35 U.S.C. 154(b) by 748 days.

(21) Appl. No.: 17/923,364

(22) PCT Filed: Jun. 15, 2021

(86) PCT No.: PCT/EP2021/066133
§ 371 (c)(1),
(2) Date: Nov. 4, 2022

(87) PCT Pub. No.: WO2022/002585
PCT Pub. Date: Jan. 6, 2022

(65) Prior Publication Data
US 2023/0201449 A1      Jun. 29, 2023

(30) Foreign Application Priority Data
Jun. 30, 2020    (EP) ..................................... 20183178

(51) Int. Cl.
A61M 5/00          (2006.01)
(52) U.S. Cl.
CPC ................................... A61M 5/002 (2013.01)
(58) Field of Classification Search
CPC .......... A61M 5/002; A61M 2005/2073; A61M 2005/3142
See application file for complete search history.

(56) References Cited

U.S. PATENT DOCUMENTS

| 5,507,730 | A | 4/1996 | Haber et al. |
| 8,597,245 | B2 | 12/2013 | Jeter et al. |
| 2013/0150800 | A1* | 6/2013 | Kemp ................. A61M 5/3204 |
| | | | 604/222 |
| 2019/0209780 | A1 | 7/2019 | Mattiuz |

FOREIGN PATENT DOCUMENTS

| EP | 2502643 A1 | 9/2012 |
| EP | 2626095 A1 | 8/2013 |

OTHER PUBLICATIONS

International Search Report and Written Opinion for Int. App. No. PCT/EP2021/066133, mailed Aug. 27, 2021.

* cited by examiner

*Primary Examiner* — Bradley J Osinski
(74) *Attorney, Agent, or Firm* — McDonnell Boehnen Hulbert & Berghoff LLP

(57) ABSTRACT
An assembly for a medicament delivery device is presented where the medicament delivery device is arranged within a package as a first subassembly extending along a longitudinal axis from a first end to a second end and a second subassembly, where the package has a first shell with a first body that extends along the longitudinal axis and defines a first chamber inside the first body that holds the first subassembly. A second shell having a second body extends along the longitudinal axis and defines a second chamber that holds the second subassembly, where the second shell is attached to the first shell by a first hinge. The first shell has a first pulling element extending along the longitudinal axis and is attached to the first subassembly and is attached to the first body by a second, where the first pulling element has a first gripper arranged at a second end of the first pulling element.

19 Claims, 7 Drawing Sheets

71     30     3

4

43     72

72b

72c

72a

PACKAGE ASSEMBLY

CROSS REFERENCE TO RELATED APPLICATIONS

The present application is a U.S. National Phase Application pursuant to 35 U.S.C. § 371 of International Application No. PCT/EP2021/066133 filed Jun. 15, 2021, which claims priority to European Patent Application No. 20183178.1 filed Jun. 30, 2020. The entire disclosure contents of these applications are herewith incorporated by reference into the present application.

TECHNICAL AREA

The present application relates to a package assembly, and specifically to a medicament delivery device package assembly.

BACKGROUND

Medicament delivery devices are generally known for the self-administration of a medicament by patients without formal medical training. As just one example, those patients suffering from diabetes may require repeated injections of insulin. Other patients may require regular injections of other types of medicaments, such as a growth hormone or biological medicaments.

To facilitate users, most self-administration medicament delivery devices are designed with many automatic functions and most of the time will contain a predetermined dosage within a pre-assembled medicament delivery device, such that users are able to carry out the medicament delivery operation with only one or two steps of manipulation of the medicament delivery device. However, there is a risk of unintentionally firing the pre-assembled medicament delivery device during shipping or transportation.

Such risk can be avoided by simply keeping the medicament delivery device as two separate subassemblies that separately contain the medicament and the power pack of the medicament delivery mechanism or simply using a cap to tightly seal an exit of the contained medicament, so that the interior pressure can keep the firing mechanism of the medicament delivery device in place. However, there will therefore be a need to facilitate the user to properly set up the medicament delivery device, such as facilitating the user to properly assemble those two separate subassemblies or to remove of the cap of the medicament delivery device. There are some package assemblies that are able to facilitate the user to properly assemble the separate subassemblies, see US2019/0209780 for an example of a medicament delivery device with a safety device.

Such safety devices work well. However, there is still room for developing more robust solutions.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "radial", "radially" refer to a direction generally perpendicular to the longitudinal direction and generally perpendicular to the transversal direction.

There is hence provided a package assembly comprising a package and a medicament delivery device; wherein the medicament delivery device is arranged within the package, the medicament delivery device comprises a first subassembly extending along a longitudinal axis from a first end to a second end; and a second subassembly extending along the longitudinal axis from a first end to a second end; and wherein the package comprises: a first shell comprising a first body, the first body extending along the longitudinal axis from a first end to a second end and defining a first chamber inside the first body; wherein the first subassembly is in the first chamber; a second shell comprising a second body, the second body extending along the longitudinal axis from a first end to a second end and defining a second chamber inside the second body; wherein the second subassembly is in the second chamber; and wherein the second shell is attached to the first shell by a hinge arranged between the second end of the second body and the second end of the first body; wherein the first shell comprises a first pulling element extending along the longitudinal axis from a first end to a second end; wherein the first subassembly is attached to the first pulling element; wherein the first pulling element is attached to the first body by a hinge arranged between the first end of the first pulling element and the first body; and wherein the first pulling element comprises a first gripper arranged at the second end of the first pulling element;

wherein the first gripper is axially fixed and pivotably attached to a counter first gripper arranged on the second subassembly.

The package assembly can facilitate an end user to properly assemble the first and the second subassemblies of the medicament delivery device, and simplify the assembly process. The end user is only asked to open the package assembly and the first and the second subassemblies of the medicament delivery device will be assembled to each other during together with the opening action.

According to one embodiment, the first pulling element comprises an elongated arm extending from the first end of the first pulling element to the second end of the first pulling element; and wherein the first gripper is arranged on the second end of the first pulling element.

According to one embodiment, the elongated arm can be a formed as a U shape; wherein the U shape is formed by two elongated arms extending from the first end of the first pulling element to the second end of the first pulling element, and a radially extending joint connecting the two elongated arms at the first end of the first pulling element.

According to one embodiment, the elongated arm can be a formed as two elongated arms extending from the first end of the first pulling element to the second end of the first pulling element.

According to one embodiment, the elongated arm can be formed as an L shape; wherein the L shape is formed an elongated arm extending from the first end of the first pulling element to the second end of the first pulling element, and an upright joint being perpendicular relative to the elongated arm and arranged at the first end of the first pulling element.

According to one embodiment, one of the first gripper and the counter first gripper is a hook or a protrusion radially extending relative to the longitudinal axis; and wherein the other one of the first gripper and the counter gripper is a recess or cut-out.

According to one embodiment, the counter first gripper is arranged on the outer surface of the second subassembly.

According to one embodiment, the first pulling element comprises a shelf; and wherein the first subassembly is engaged with the shelf by a press fit or a form fit arranged between the outer surface of the first subassembly and the shelf. According to one embodiment, the first pulling element comprises an elongated body portion; wherein the shelf comprises a shelf body, the shelf body extending along the longitudinal axis from a first end to a second end; wherein the shelf is attached to the elongated body portion by an engagement between an engaging member arranged on the shelf and a counter engaging member arranged on the body portion of the first pulling element; and wherein one of the engaging member and the counter engaging member is a longitudinally extending rib; and wherein the other one of the engaging member and the counter engaging member is a longitudinally extending slot.

According to one embodiment, the second shell comprises a support extending along the longitudinal axis from a first end to a second end; wherein the support is attached to the second body by a hinge arranged between the first end of the support and the first end of the second body; and wherein the second subassembly is attached to the support.

According to one embodiment, the second shell comprises a second pulling element extending along the longitudinal axis from a first end to a second end; wherein an attaching member is arranged at the first end of the second pulling element and is axially fixed and pivotably attached to a counter attaching member arranged on the second body; and wherein a second gripper is arranged at the second end of the second pulling element and is axially fixed and pivotably attached to a counter second gripper; and wherein the counter second gripper is fixedly connected to the first subassembly of the medicament delivery device.

According to one embodiment, the second pulling element comprises an elongated arm, the elongated arm can be a formed as a U shape; wherein the U shape is formed by two elongated arms extending from the first end of the second pulling element to the second end of the second pulling element, and a radially extending joint connecting the two elongated arms at the first end of the second pulling element.

According to one embodiment, the elongated arm can be a formed as two elongated arms extending from the first end of the second pulling element to the second end of the second pulling element.

According to one embodiment, the elongated arm can be formed as an L shape; wherein the L shape is formed an elongated arm extending from the first end of the second pulling element to the second end of the second pulling element, and an upright joint being perpendicular relative to the elongated arm and arranged at the second end of the second pulling element.

According to one embodiment, the elongated arm can be formed by an elastic member, such as a tension spring; wherein the one end of the tension spring is fixed to the second shell and the other end of the tension spring is fixedly connected with the first subassembly of the medicament delivery device; so that the movement of the first shell relative to the second shell causes the tension spring to pull the first subassembly towards the second subassembly.

According to one embodiment, wherein the counter second gripper is arranged on an outer surface of the first subassembly.

According to one embodiment, the counter second gripper is arranged on the shelf.

According to one embodiment, one of the second gripper and the counter second gripper is a hook or a protrusion radially extending relative to the longitudinal axis; and wherein the other one of the second gripper and the counter second gripper is a recess or cut-out.

According to one embodiment, the counter attaching member is arranged on the inner surface of the second chamber.

According to one embodiment, the counter attaching member is arranged on the support.

According to one embodiment, one of the attaching member and the counter attaching member is a hook or a protrusion radially extending relative to the longitudinal axis; and wherein the other one of the attaching member and the counter attaching is a recess or cut-out.

According to one embodiment, the second subassembly of the medicament delivery device comprises a cap, the cap is detachably arranged on the first end of the second subassembly of the medicament delivery device.

According to one embodiment, the second shell comprises a block; and wherein the block is engaged with the cap by a press fit or form fit arranged in between.

According to one embodiment, the second subassembly comprises a medicament container holder configured to releasably receive a medicament container, the medicament container containing a medicament; wherein the medicament container is placed into the medicament container holder by the end user.

According to one embodiment, the second subassembly comprises a medicament container containing a medicament.

According to one embodiment, the second subassembly comprises a medicament delivery member.

According to one embodiment, the second subassembly comprises a medicament container holder configured to receive a medicament container, the medicament container containing a medicament.

According to one embodiment, the medicament container can be a syringe arranged with a needle or a delivery nozzle; or a cartridge that can be attached with a needle or a delivery nozzle by the end user.

According to another embodiment, the package of the package assembly can be simply modified to be used with a medicament delivery device that is preassembled and with a detachable cap. Such a package assembly can facilitate the end user to properly remove the detachable cap from the medicament delivery device together with the operation of opening the package assembly. There is hence provided a package assembly comprising a package and a medicament delivery device; wherein the medicament delivery device comprises a housing extending along a longitudinal axis from a first end to a second end; and a detachable cap arranged at the first end of the housing of the medicament delivery device; wherein the package comprises: a cover having a cover body, the cover body extending along the longitudinal axis from a first end to a second end; a shell having a shell body, the shell body extending along the longitudinal axis from a first end to a second end and defining a chamber inside the shell; wherein the medicament delivery device is in the chamber; wherein the shell body is attached to the cover body by a hinge arranged between the second end of the shell body and the second end of the cover body; wherein the cover comprises a first pulling element extending along the longitudinal axis from a first end to a second end; wherein the first pulling element is attached to the cover body by a hinge between the first end of the first pulling element and the first end of the cover body; wherein the first pulling element comprises a first gripper arranged at the second end of the first pulling element; wherein the first gripper is axially fixed and pivotably attached to a counter first gripper, the counter first gripper is arranged on the housing of the medicament delivery device; and wherein the shell comprises a block engaged with the cap; wherein the engagement between the block and the cap is a press fit or form fit.

According to one embodiment, the shell comprises a support extending along the longitudinal axis from a first end to a second end; wherein the support is arranged within the chamber; wherein the support is attached to the shell body by a hinge between the first end of the support and the first end of the shell body; and wherein the medicament delivery device is arranged on the support.

According to one embodiment, the block is arranged on inner surface of the support.

According to one embodiment, the counter first gripper is arranged on the outer surface of the medicament delivery device.

According to one embodiment, one of the first gripper and the counter first gripper is a hook or a transversal protrusion; and wherein the other one of the first gripper and the counter first gripper is a recess or cut-out.

According to one embodiment, the medicament delivery device, both preassembled or with two subassemblies, can be a safety syringe, an auto injector, a pen injector, an inhalation device, an on-body device or a medical sprayer.

Other aspects, features, and advantages will be apparent from the summary above, as well as from the description that follows, including the figures and the claims.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

Embodiments of the present disclosure will now be described, by way of example only, with reference to the accompanying drawings, in which.

DETAILED DESCRIPTION

Figure 1A:
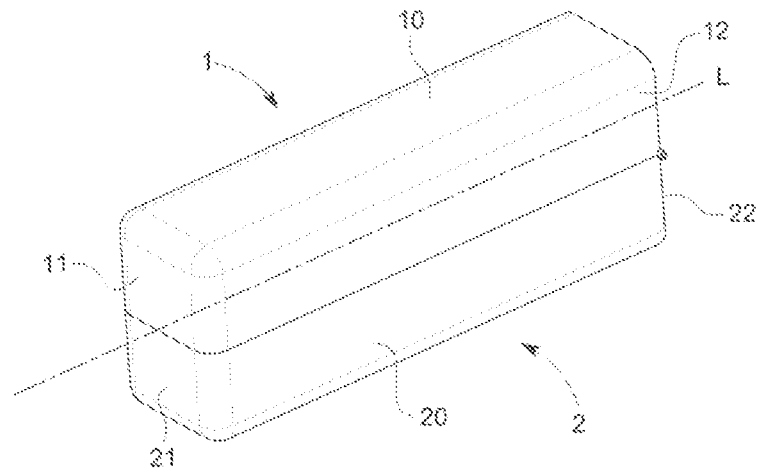
FIGS. 1A and 1B display a perspective view of a package assembly of the present disclosure.
Figure 1B:
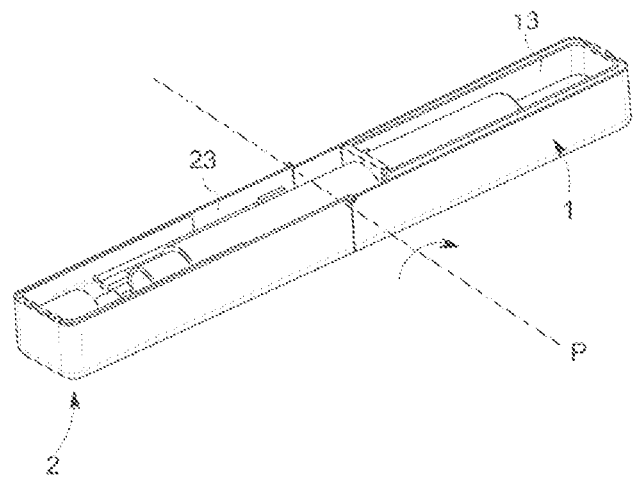
Figure 6A:
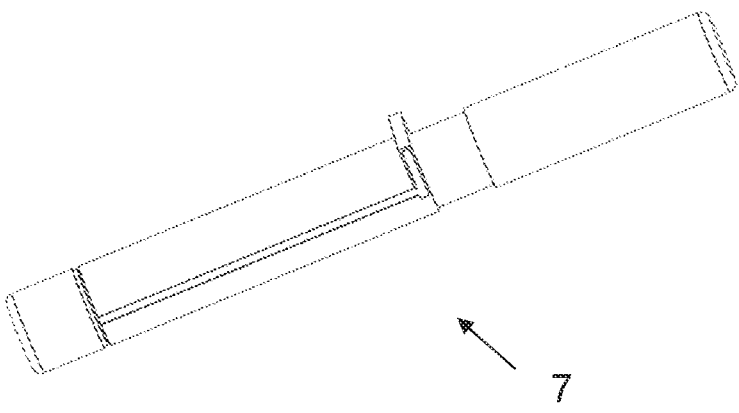
FIGS. 6A and 6B display a perspective view of a medicament delivery device with a first subassembly and a second subassembly of the package assembly of FIG. 1A-1B.
Figure 6B:
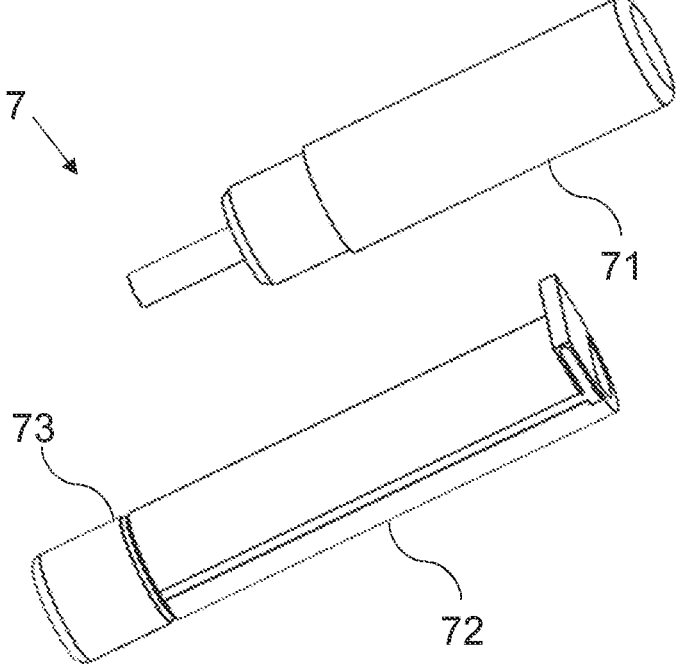

FIG. 1A-1B illustrate a package assembly comprising a package and a medicament delivery device 7, the medicament delivery device 7 is shown in FIG. 6A-6B. The package comprises a first shell 1. The first shell 1 comprises a first body 10, the first body 10 extending along a longitudinal axis L from a first end 11 to a second end 12. The first body comprises a base part, the base part longitudinally extending parallel relative to the longitudinal axis L; and a wall part, the wall part longitudinally extending along the longitudinal axis L and arranged at least partially perpendicular to the longitudinal axis L, the base part and a wall part surround an interior space as a first chamber 13 inside the first body 10 for receiving at least a partial portion of a first subassembly of the medicament delivery device 7. The package comprises a second shell 2. The second shell 2 comprises a second body 20, the second body 20 extending along the longitudinal axis L from a first end 21 to a second end 22. The second body comprises a base part, the base part longitudinally extending parallax relative to the longitudinal axis L; and a wall part, the wall part longitudinally extending along the longitudinal axis L and arranged at least partially perpendicular to the longitudinal axis L. The base part and a wall part surround an interior space as a second chamber 23 inside the second body 20 for receiving at least a partial portion of a second subassembly of the medicament delivery device 7. The second shell 2 is attached to the first shell 1 by a hinge arranged between the second end 22 of the second body 20 and the second end 12 of the first body 10.

FIG. 1A shows the package assembly in a closed state. When the package assembly is in the closed state, the first shell 1 is placed on the second shell2, such that the first end 11 of the first shell 1 is aligned with or close to the first end 21 of the second shell 2. The first body 10 and the second body 20 can be formed as a rectangular shape, oval shape or circular shape, depending on the shape and size of the medicament delivery device that is retained by the package.

In a preferred embodiment, the first end of the first and the second shell are designed to prevent contamination from the environment, so the first end of the first and the second shell comprises a sealing wall at least partially perpendicular to the longitudinal axis L. On the other hand, instead of the sealing wall, the second end 12 of the first shell 1 and the second end 22 of the second shell 2 may be and open end, so that the movement of the first and the second subassembly of the medicament delivery device 7 will not be blocked; when the package assembly is in the close state, the second end 12 of the first shell 1 and the second end 22 of the second shell 2 are aligned with each other so one close loop shape opening end is formed, a separate seal, e.g. a cap, a membrane or a foil, can be provided to seal the opening end, so that the contamination from the environment can be prevented. The first end 11 of the first shell 1 is aligned with the first end 21 of the second shell 2, such that the first chamber 13 and the second chamber 23 are sealed within the interior space between the first body 10 and the second body.

It should be noted that, if the package assembly is packed in a sealable bag, such that the environment contamination can be prevented by the sealable bag, then the sealing walls and the separate seal may be removed.

The package assembly is configured to be manufactured, preassembled and then delivered to an end user in the closed state. When the end user, for example the patient, caregiver, doctor or pharmacist, plans to use the medicament delivery device 7 contained within the package of the package assembly, the end user needs to open the package by rotating the first shell 1 relative to the second shell 2 along a pivot axis P, the pivot axis P is set on the hinge between the second end 11 of the first shell 1 and the second end of the second shell 21; then the package assembly is opened to an open state, as shown in FIG. 1B.

Figure 2A:
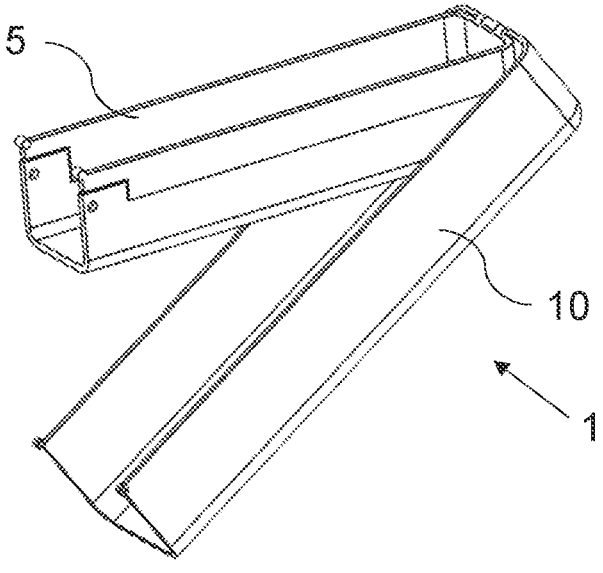
FIGS. 2A and 2B display a perspective view of a first shell of the package assembly of FIG. 1A-1B.
Figure 2B:
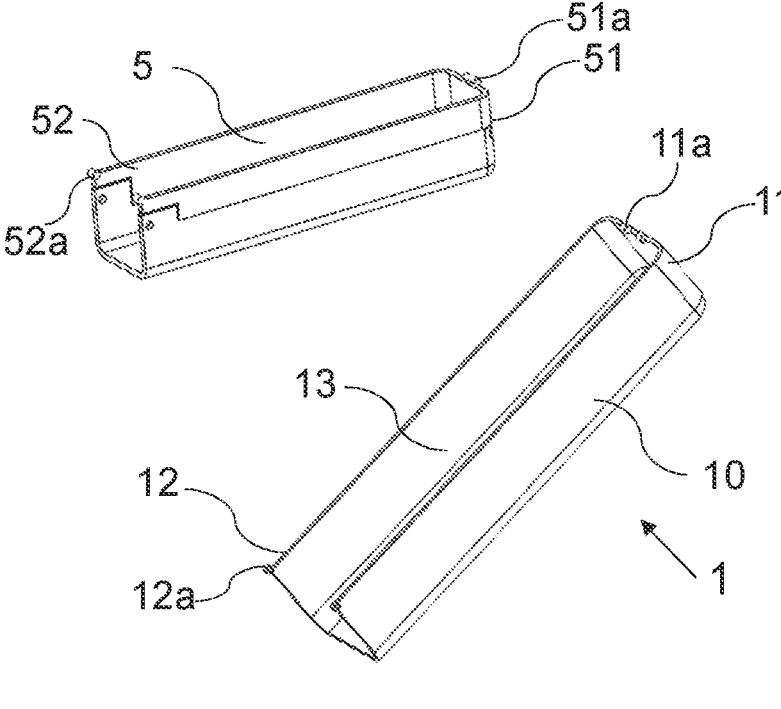

FIG. 2A-2B illustrate the first shell 1. The first shell 1 comprises a first connecting member 12*a* arranged on the second end 12 of the first shell 1 and configured to pivotally connect to a second connecting member 22*a* arranged on second end 22 of the second shell 2, as shown in FIG. 3B, and defines the hinge, such that the first shell 1 is able to rotate in relation to the pivot axis P from the closed state of the package assembly to the open state of the package assembly.

Figure 4:
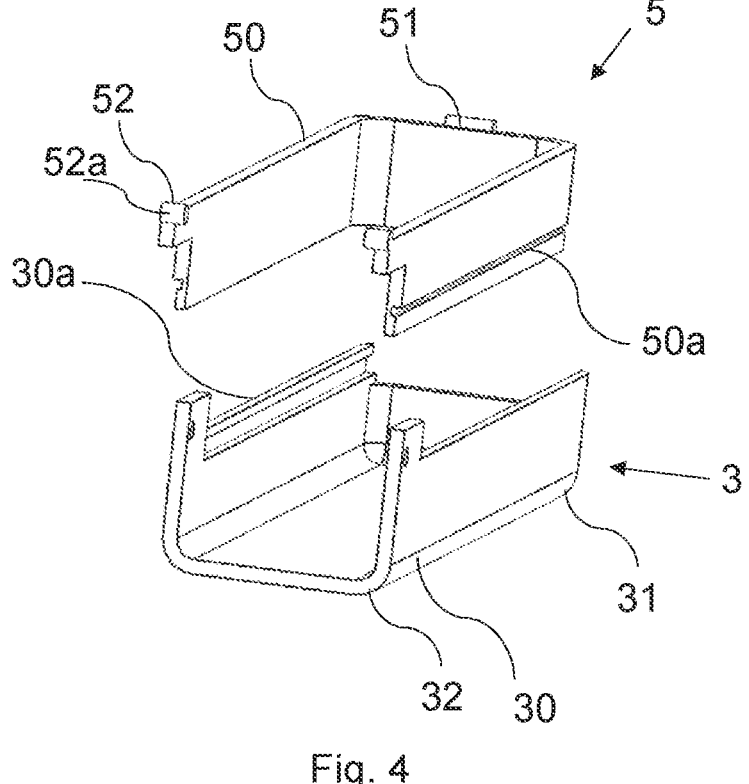
FIG. 4 displays a perspective view of a first pulling element of the package assembly of FIG. 1A-1B.

The first shell 1 comprises a first pulling element 5. As shown in FIG. 4, the first pulling element 5 is arranged within the first chamber 13. The first pulling element 5 comprises an elongated body portion 50 extending along the longitudinal axis L from a first end 51 to a second end 52. The first pulling element 5 further comprises a first pulling connecting member 51*a* arranged on the first end 51 of the first pulling element 5 and configured to pivotally engage with a counter first pulling connecting member 11*a* which is arranged on the first end 11 of the first shell 1. The first pulling element 5 is therefore axially fixed but pivotally movable in relation to the first shell 1. The first pulling element 5 further comprises a first gripper 52*a* configured to grip and pull the second subassembly 72 of the medicament delivery device 7, as will be explained in detail later.

Figure 7:
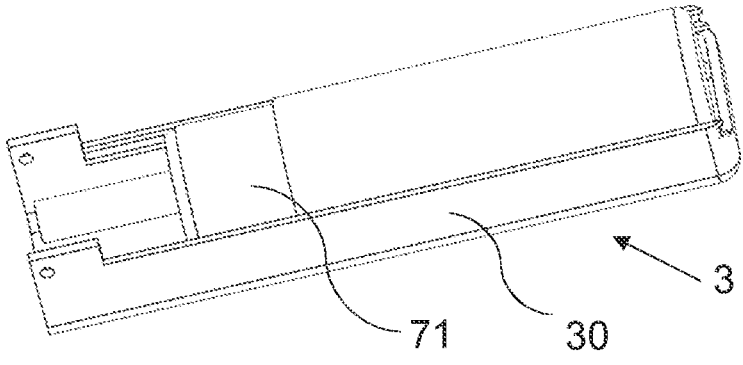
FIG. 7 displays a perspective view of a connection between the first subassembly of the medicament delivery device and the shelf of the package assembly of FIG. 1A-1B.

In a preferred embodiment, the first pulling element 5 comprises a shelf 3, as shown in FIG. 4, for attaching the first subassembly 71 of the medicament delivery device 7 to the first pulling element, as shown in FIG. 7, and therefore to the first shell 1.

The shelf 3 comprises a shelf body 30 extending along the longitudinal axis L from a first end 31 to a second end 32. The elongated body portion 50 of the first pulling element 5 comprises a first pulling engaging member 50*a* arranged on the outer surface of the elongated body portion 50. The first pulling engaging member 50*a* is configured to be axially slidable (along the longitudinal axis L) and to engage with a counter engaging member 30*a* arranged on an inner surface of the shelf body 30 of the shelf 3. Preferably, the first pulling engaging member 50*a* can be a longitudinal groove and the counter engaging member 30*a* can be a longitudinal ledge.

The first pulling engaging member 50*a* is axially slidably engaged with the counter engaging member 30*a*, the shelf 3 is therefore axially slidable but transversely restricted in relation to the first pulling element 5. Further, since the first pulling element 5 is axially fixed but pivotally movable in relation to the first shell 1, the shelf 3 is also axially slidable but transversely restricted in relation to the first shell 1.

It should be noted that, alternatively, the first pulling engaging member can be arranged on the inner surface of the elongated body portion, and the counter engaging member can be arranged on the outer surface of the shelf body.

In a preferred embodiment, the shelf body 30 may comprise a partially surrounding wall for receiving the first subassembly 71 of the medicament delivery device 7. The first subassembly 71 of the medicament delivery device 7 can be attached to the shelf body 30 by a form-fit, such as a protrusion on the inner surface of the shelf body that is engaged with a recess on the outer surface of the first subassembly 71; or press-fit, such that the shelf body 30 comprises a narrower width than a width of the first subassembly 71, so that the first subassembly 71 of the medicament delivery device can be clamped on the shelf body 30. It should be noted that, alternatively, the first subassembly can also be directly attached to the elongated body portion 50 of the first pulling element 5 by the form-fit or press-fit attachment; in this embodiment, the shelf 3 may be removed from the design, the first pulling element 5 may grip and pull the second subassembly 72, as will be explained in detail later, to assembly the second subassembly 72 with the first subassembly 71.

Figure 3A:
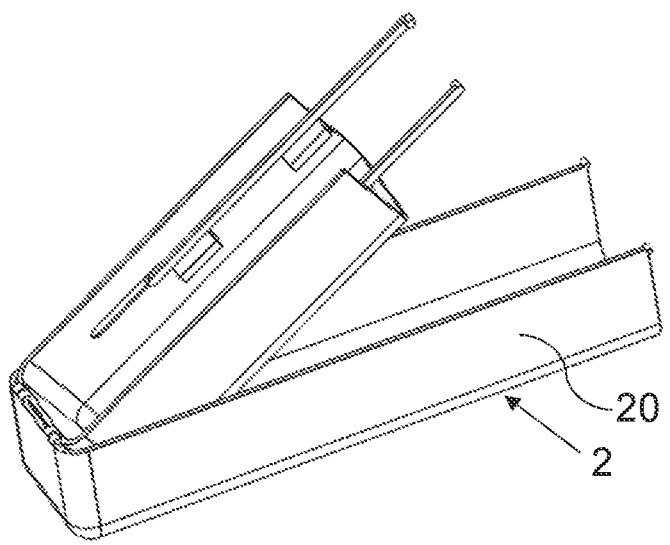
FIGS. 3A and 3B display a perspective view of a second shell of the package assembly of FIG. 1A-1B.
Figure 3B:
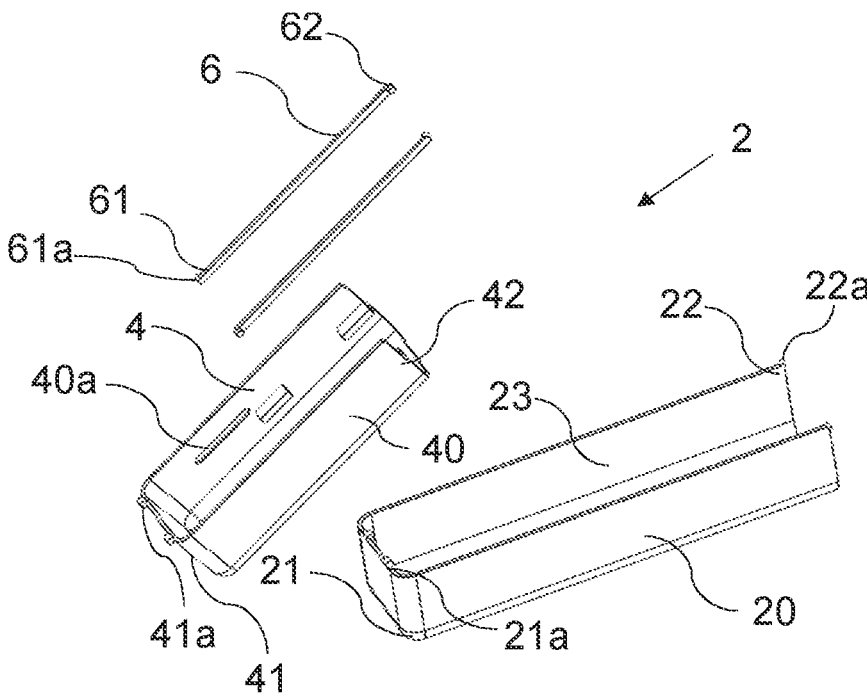

FIG. 3A-3B illustrate the second shell 2. The second shell 2 is configured to receive the second subassembly 72 of the medicament delivery device 7. In a preferred embodiment, the second shell 2 comprises a support 4, the support 4 extending along the longitudinal axis L from a first 41 end to a second end 42; wherein the support 4 is at least partially arranged in the second body 20 and is attached to the second body 20 by a hinge arranged between the first end of the support 4 and the first end 21 of the second shell; for example, the second shell comprises a connecting member 21*a* arranged on the first end 21 and the support 4 comprises a counter connecting member 41*a* arranged on the first end 41 of the support 4, and the connection between the connecting member 21*a* and the counter connecting member 41*a* defines the hinge.

The support 4 is arranged for attaching the second subassembly 72 of the medicament delivery device 7 to the second shell 2, and to guide the movement of the second subassembly 72 when the second subassembly 72 is being pulled by the first pulling element 5; in a preferred embodiment, the support 4 comprises a partially surrounding wall 40 and defining an interior space, so that the support 4 can more easily guide and support the second subassembly 72.

It should be noted that the second subassembly 72 can also be fixed directly to the second body 20 of the second shell 2 without the support 4. In this case, an elastic element, e.g. a coil spring or a flexible arm, may be arranged between the second body 20 and the second subassembly 72; the elastic element can be in a tension state when the package assembling is in the close state; so that when the second end of the second subassembly 72 has been lifted by the first pulling element 5, the elastic element can extend and support the second subassembly to align with the first subassembly 71. When the package moving to its open state, the assembled medicament delivery device being guided and pulled by the package and also press the elastic element back to its tension state.

In another preferred embodiment, the second shell 2 further comprises a second pulling element 6 arranged at least partially within the second camber 23, the second pulling element 6 extending along the longitudinal axis L from a first end 61 to a second end 62. The second pulling element 6 can be a pair of pulling rods as shown in FIG. 3B, or be formed as an L shape; wherein the second pulling element 6 is formed with elongated arms extending from the first end of the second pulling element to the second end of the second pulling element, and a upright joint that is perpendicular relative to the elongated arm and arranged at the first end of the second shell 2.

The second pulling element 6 comprises an attaching member 61a, the attaching member 61a is arranged at the first end 61 of the second pulling element 6 and is axially fixed and pivotably attached to a counter attaching member arranged on the second shell 2. When the second shell 2 has the support 4, the counter attaching member 40a can be arranged on the support 4 or the inner surface of the partially surrounding wall 40 of the support 4, as shown in FIG. 3B.

Figure 5:
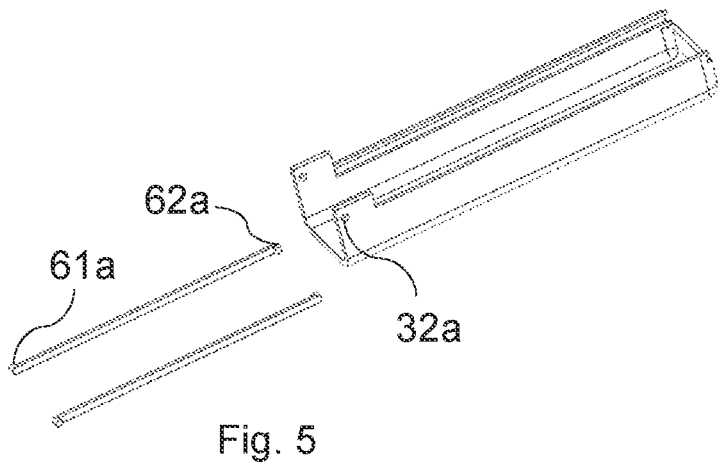
FIG. 5 displays a perspective view of a shelf and the first pulling element of the package assembly of FIG. 1A-1B.

The second pulling element 6 comprises a second gripper 62a arranged at the second end 62 of the second pulling element 6 and axially fixed and pivotably attached to a counter second gripper 32a. The counter second gripper 32a is fixedly arranged on the second end 32 of the shelf body 30, as shown in FIG. 5.

As mentioned above, the package assembly is configured to store the medicament delivery device 7 as shown in FIG. 6A-6B. The medicament delivery device extends along the longitudinal axis L from a proximal end, which is the end that will be pointed at the medicament delivery site during the operation of the medicament delivery sequence, to a distal end, which is the end that is further away from the medicament delivery site during the operation of the medicament delivery sequence.

The medicament delivery device 7 may comprise the first subassembly 71 extending along a longitudinal axis L from a first end (proximal end) to a second end (distal end). Preferably the first subassembly 71 is configured to contain an energy source which is configured to actuate a medicament delivery operation so that a contained medicament can be delivered to a medicament delivery site; the second subassembly 72 extending along a longitudinal axis L from a first end (proximal end) to a second end (distal end). Preferably the second subassembly 72 is configured to contain a medicament container that contains the medicament with predetermined volume and a medicament delivery member; and a detachable cap 73 arranged on the first end of the second subassembly 72 and is configured to completely cover the medicament delivery member when the cap 73 is attached to the first end of the second subassembly 72, as shown in FIG. 6A-6B. The medicament delivery device 7 is operable for a medicament delivery sequence once the first subassembly 71 and the second subassembly 72 have been assembled together.

The first subassembly 71 comprises an interface and the second subassembly 72 comprises a counter interface, such that the first subassembly 71 can be fixed to the second subassembly 72 through the engagement between the interface and the counter interface by axially pushing the first and the second subassemblies of the medicament delivery device 7 towards each other. Since this aspect is not a focus of the present disclosure, and since many different variations of such connection functionality and the interface structure can be realised, this feature will not be discussed in any further detail herein.

As mentioned above, in a preferred embodiment, the first subassembly 71 is arranged on the shelf 3, as shown in FIG. 7. The first subassembly 71 of the medicament delivery device 7 is axially fixed but transversely releasable in relation to the shelf 3, such that the first subassembly 71 of the medicament delivery device 7 is proximally slidable together with the shelf 3 along the longitudinal axis L.

Figure 8:
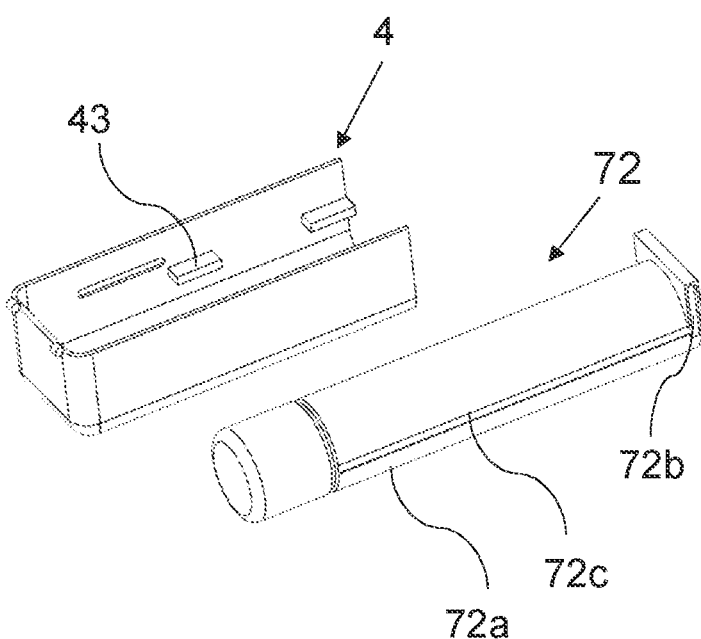
FIG. 8 displays a perspective view of a support of the second shell and the second subassembly of the medicament delivery device of the package assembly of FIG. 1A-1B.
Figure 9:
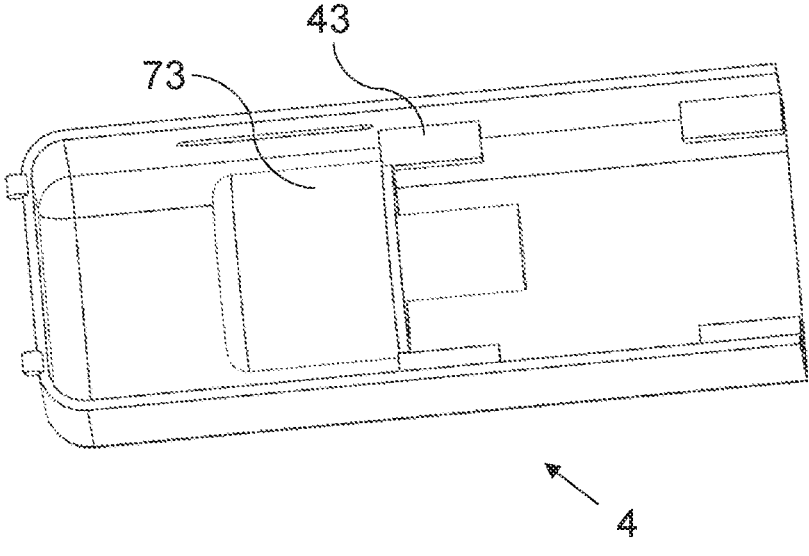
FIG. 9 displays a perspective view of a block arranged on the second shell and the interaction with a cap of the medicament delivery device of the package assembly of FIG. 1A-1B.
Figure 10:
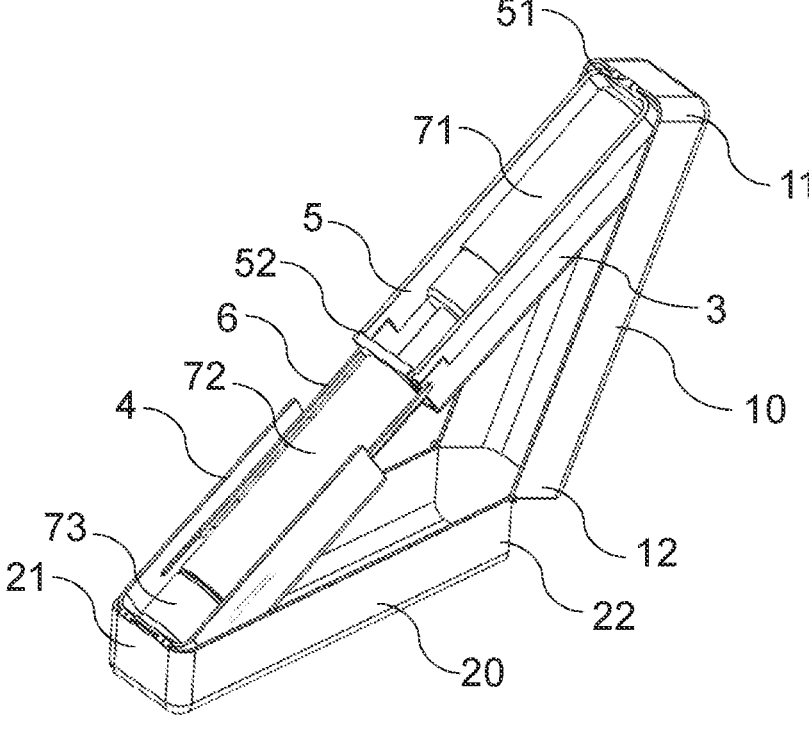
FIG. 10 displays a perspective view of the package assembly of FIG. 1A-1B.

As shown in FIG. 8, the second subassembly 72 and the cap 73 is at least partially received in the second chamber 23 of the second shell 2 (by the support 4 in a preferred embodiment). The second subassembly 72 comprises a second elongated body 72a, a counter first gripper 72b arranged on the second end of the second subassembly 72 of the medicament delivery device 7, and a second engaging member 72c arranged on the outer surface of the second elongated body 72a. The second engaging member 72c is configured to axially slidably engage with a counter second engaging member 43 that is arranged on the inner surface of the partial surrounding wall 40 of the support 4. Preferably, the second engaging member 72c is a longitudinal slot and the fourth counter engaging member 43 is a radial inwardly extending protrusion. The second subassembly 72 is therefore axially slidable but transversely restricted in relation to the support 4.

The counter first gripper 72b of the second subassembly 72 of the medicament delivery device 7 is configured to hingedly engage with a first gripper 52a arranged on the second end 52 of the first pulling element 5. Preferably, the counter first gripper 72b of the second subassembly 72 of the medicament delivery device 7 is a transverse slot and the first gripper 52a is a radially inwardly extending rib, such that the counter first gripper 72b is axially fixed but transversely movable in relation to the second end 52 of the first pulling element 5.

Further, the cap 73 of the medicament delivery device 7 may be bidirectionally or unidirectionally axially fixed to the support 4 in a predetermined position in relation to the support 4. The cap 73 may comprise a diameter of its outer contour, such diameter is larger than a radial width defined by the counter second engaging member 43. The counter second engaging member therefore acts as a block for the cap 73. Once the cap 73 is distally moved together with the second subassembly 72 and the outer contour of the cap 73 meets the front edge of the counter second engaging member 43, or the block, the further distal movement of the cap 73 is prevented.

It should be noted that, the block for the cap 73 can also be arranged on the inner surface of the second chamber 23. The engagement between the block and the cap 73 can alternatively be a form-fit as described above (a protruding edge engaging with the distal edge of the cap 73), or a press-fit, such that the second chamber 23 or the support 4 comprises a narrower diameter so that the cap 73 may be clamped by the second inner surface of the second chamber 23 or the support 4.

As mentioned above, the package assembly is configured to contain the medicament delivery device 7 and be delivered to an end user with the configuration that the first shell 1 is in the first position, as shown in FIG. 1A. To keep the medicament delivery device 7 from contamination, there may be a protective cover configured to cover on both the second end 12 of the first shell 1 and second end 22 of the shell 2. The first subassembly 71 is in the first chamber 13 of the first shell 1 and the second subassembly 72, arranged with the cap 73 on its proximal end, and is in the second chamber 23 of the second shell 2. The first shell 1 is arranged on top of the second shell 2 or covering the second shell 2, the first subassembly 71 is therefore separate to the second subassembly 72.

In a preferred embodiment, when the end user of the medicament delivery device 7 plans to use the medicament delivery device 7, he/she is required to open the package assembly by rotating the first shell 1 in relation to the pivot axis P. The shelf 3 is fixedly engaged with the first pulling element 5 by the engagement between the first pulling engaging member and the counter engaging member, and the counter second gripper 32a is hingedly engaged with the attaching member 62a; the rotation of the first shell 1 causes the first pulling element 5 and the shelf 3 pivot relative to the first body 10 of the first shell 1, because the hinge between the first end 51 of the first pulling element 5 and the first body 10, and the second end 52 of the first pulling element 5 is hingely engaged with the second end of the second subassembly 72; the pivotal movement of the first pulling element 5 and the shelf 3 makes the first subassembly 71 pivot relative to the first body 10.

Upon rotating of the first shell 1, the engagement between the second end 52 of the first pulling element 5 and the second end of the second subassembly 72 causes the second end of the second subassembly 72 be lifted by the pivotal movement of the first pulling element 5, so that the second subassembly 72 also pivots relative to the second body 20 of the second shell.

At the same time, the rotation of the first shell 1 also causes the second end 62 of the second pulling element 6 to be lifted by the pivotal movement of the shelf 3, which is caused by the pivotal movement of the first pulling element 5 and the first shell 1. Such lifting movement of the second pulling element 6 causes the attaching member 61a to axially and transversely slide and pivotally move in relation to counter attaching member 40a, such that it also causes the pivotal movement of the support 4 in relation to the second shell 2 through the engagement between the attaching member 61a and the counter attaching member 40a of the support 4. The shelf 3 is only engaged with the second pulling element 6 through the engagement between the second gripper 62a and the counter second gripper 32a, the pivotal movement of the support 4 together with the second pulling element 6 causes the transverse movement of the second end 32 of the shelf 3. Such transverse movement of the second end 32 of the shelf 3 causes further pivotal movement of the first pulling element 5 in relation to the first shell 1 through the transversely fixed engagement between the first pulling engaging member 50a and the counter engaging member 30a between the first pulling element 5 and the shelf 3.

When the attaching member 61a is engaged with the end edge of the counter attaching member 40a, the further distal axial movement of the second pulling member 6 is prevented. The further rotational movement of the first shell 1 thereby causes the second pulling element 6 to proximally pull the shelf 3 together with the first subassembly 71 through the engagement between the second gripper 62a and the counter second gripper 32a.

At the same time, the first pulling element 5 is pivotally but axially fixedly arranged to the first shell 1, the first pulling element 5 is therefore pivotally moved together with the first shell 1. Such pivotal movement of the first pulling element 5 is turned into an axial distally pulling movement of the second subassembly 72, due to the axially fixed hinge engagement between the first gripper 52a and the counter first gripper 72b of the second subassembly 72 of the medicament delivery device 7, such that the second subassembly 72 is pulled towards the first subassembly 71.

The cap 73 is axially fixed to the support 4 by the block in a predetermined position (determined by the location of the block); such a distal pulling movement of the second subassembly 72 of the medicament delivery device 7 detaches the cap 73 from the second subassembly 72 of the medicament delivery device 7.

The proximal pulling movement of the first subassembly 71 and the distal pulling movement of the second subassembly 72 cause the first and the second subassembly of a medicament delivery device 7 to be assembled together when the first shell 1 is moved from the first position to the second position. When the first shell 1 reaches the second position, as shown in FIG. 1B, the medicament delivery device 7 is thereby properly assembled and the cap 73 has been detached from the medicament delivery device 7. The medicament delivery device 7 is then ready for carrying out the medicament delivery sequence. It should be noted that, alternatively, if in the embodiment that the shelf 3 has been removed from the design of the package, the first subassembly may be fixed to the first pulling element, meaning that there will be no proximal pulling movement of the first subassembly, the distal pulling movement of the second subassembly, when the first shell is rotating, causes the second subassembly to be assembled to the first subassembly.

The first gripper 52a is axially fixed but transversely movable in relation to the counter first gripper 72b, the end user is therefore able to remove the medicament delivery device 7 from the package assembly by transversely pulling the medicament delivery device 7 away from the package.

The package of the package assembly may be modified for using with a medicament delivery device without a cap, by simply removing the block. In such a case, the package preferably has a sterile cover, e.g. by being wrapped in foil or sealed in a bag.

The package of the package assembly may be used with a medicament delivery device that has a prefilled medicament container, e.g. a prefilled syringe; the prefilled medicament container is arranged at the second subassembly.

The package of the package assembly may be used with a medicament delivery device that the end user is able to put into an independent medicament container, namely the medicament delivery device may be delivered to the end user without a prefilled medicament container. The end user can load a medicament container first; for example, loading the medicament container through the second end of the second shell and the second subassembly; then opening the package for properly assembling the first subassembly and the second subassembly.

The package of the package assembly may be modified for use with a medicament delivery device which is manufactured as one single piece, namely the medicament delivery device does not require the end user to assemble two subassembly parts. In this case, the package can be modified for removing a detachable cap of the medicament delivery device. In this case, the medicament delivery device should be arranged at least partially in the second chamber and the cap should be aligned with the block on the second shell. The first shell can be modified as just a cover or lid with only a small interior space for at least partially receiving the first pulling element, or even with no interior space, in which case the first pulling element can be arranged partially within the second chamber. The first gripper, in this case, should grip on a counter first gripper that is arranged on the outer surface of the medicament delivery device. The rest of the arrangement of the package can remain the same as described above.

The present disclosure has been described above with reference to a few examples. However, as is readily appreciated by a person skilled in the art, other embodiments than the ones disclosed above are equally possible within the scope of the present disclosure concept, as defined by the appended claims.

The invention claimed is:

1. A package assembly comprising a package and a medicament delivery device; wherein the medicament delivery device is arranged within the package, the medicament delivery device comprises a first subassembly extending along a longitudinal axis from a first end to a second end; and a second subassembly extending along the longitudinal axis from a first end to a second end; and wherein the package comprises:

a first shell comprising a first body, the first body extending along the longitudinal axis from a first end to a second end and defining a first chamber inside the first body;

wherein the first subassembly is in the first chamber;

a second shell comprising a second body, the second body extending along the longitudinal axis from a first end to a second end and defining a second chamber inside the second body; wherein the second subassembly is in the second chamber; and wherein the second shell is attached to the first shell by a hinge arranged between the second end of the second body and the second end of the first body;

wherein the first shell comprises a first pulling element extending along the longitudinal axis from a first end to a second end; wherein the first subassembly is attached to the first pulling element;

wherein the first pulling element comprises a shelf;

wherein the first subassembly is engaged with the shelf by a press fit or a form fit arranged between the outer surface of the first subassembly and the shelf;

wherein the first pulling element is attached to the first body by a hinge arranged between the first end of the first pulling element and the first body; and wherein the first pulling element comprises a first gripper arranged at the second end of the first pulling element;

wherein the first gripper is axially fixed and pivotably attached to a counter first gripper arranged on the second subassembly.

2. The package assembly as claimed in claim 1, wherein the first pulling element comprises an elongated arm extending from the first end of the first pulling element to the second end of the first pulling element; and wherein the first gripper is arranged on the second end of the first pulling element.

3. The package assembly as claimed in claim 1, wherein one of the first gripper and the counter first gripper is a hook or a protrusion radially extending relative to the longitudinal axis; and wherein the other one of the first gripper and the counter gripper is a recess or cut-out.

4. The package assembly as claimed in claim 1, wherein the counter first gripper is arranged on the outer surface of the second subassembly.

5. The package assembly as claimed in claim 1, wherein the first pulling element comprises an elongated body portion; wherein the shelf comprises a shelf body, the shelf body extending along the longitudinal axis from a first end to a second end; wherein the shelf is attached to the elongated body portion by an engagement between an engaging member arranged on the shelf and a counter engaging member arranged on the body portion of the first pulling element; and wherein one of the engaging member and the counter engaging member is a longitudinally extending rib; and wherein the other one of the engaging member and the counter engaging member is a longitudinally extending slot.

6. The package assembly as claimed in claim 1, wherein the second shell comprises a support extending along the longitudinal axis from a first end to a second end; wherein the support is attached to the second body by a hinge arranged between the first end of the support and the first end of the second body; and wherein the second subassembly is attached to the support.

7. The package assembly as claimed in claim 1, wherein the second shell comprises a second pulling element extending along the longitudinal axis from a first end to a second end; wherein an attaching member is arranged at the first end of the second pulling element and is axially fixed and pivotably attached to a counter attaching member arranged on the second shell; and wherein a second gripper is arranged at the second end of the second pulling element and is axially fixed and pivotably attached to a counter second gripper; and wherein the counter second gripper is fixedly connected to the first subassembly of the medicament delivery device.

8. The package assembly as claimed in claim 7, wherein the counter second gripper is arranged on an outer surface of the first subassembly.

9. The package assembly as claimed in claim 7, wherein the counter second gripper is arranged on the shelf.

10. The package assembly as claimed in claim 7, wherein one of the second gripper and the counter second gripper is a hook or a protrusion radially extending relative to the longitudinal axis; and wherein the other one of the second gripper and the counter second gripper is a recess or cut-out.

11. The package assembly as claimed in claim 7, wherein the counter attaching member is arranged on the inner surface of the second body.

12. The package assembly as claimed in claim 7, wherein the counter attaching member is arranged on a support pivotedly attached to the second body.

13. The package assembly as claimed in claim 7, wherein one of the attaching member and the counter attaching member is a hook or a protrusion radially extending relative to the longitudinal axis; and wherein the other one of the attaching member and the counter attaching is a recess or cut-out.

14. The package assembly as claimed in claim 1, wherein the second subassembly of the medicament delivery device comprises a cap, the cap being detachably arranged on the first end of the second subassembly of the medicament delivery device.

15. A package assembly comprising:

a package containing a medicament delivery device that comprises a first subassembly and a second subassembly where each subassembly has a first end to a second end and a second subassembly extending along a longitudinal axis, where the package comprises:

a first shell comprising a first body that extends the longitudinal axis from a first end to a second end, where a first chamber is located inside the first body and the first subassembly is in the first chamber; and a second shell comprising a second body that extends along the longitudinal axis from a first end to a second end, where a second chamber is located inside the second body and the second subassembly is in the second chamber, wherein the second shell is attached to the first shell by a first hinge, wherein the first shell further comprises a first pulling element extending along the longitudinal axis from a first end to a second end, the first subassembly is attached to the first pulling element and the first pulling element is attached to the first body by a second hinge arranged between the first end of the first pulling element and the first body, wherein the first pulling element comprises a first gripper arranged at the second end of the first pulling element, where the first gripper is axially fixed and pivotably attached to a counter first gripper arranged on the second subassembly, wherein the second shell further comprises a support extending along the longitudinal axis from a first end to a second end, where the support is attached to the second body by a third hinge arranged between the first end of the support and the first end of the second body and where the second subassembly is attached to the support.

16. The package assembly as claimed in claim 15, where the second shell further comprises a second pulling element having an attaching member arranged at a first end of the second pulling element that is axially fixed and pivotably attached to a counter attaching member arranged on the second shell.

17. The package assembly as claimed in claim 16, wherein a second gripper is arranged on the second pulling element and is axially fixed and pivotably attached to a counter second gripper that is fixedly connected to the first subassembly of the medicament delivery device.

18. The package assembly as claimed in claim 17, wherein one of the second gripper and the counter second gripper is a hook or a protrusion radially extending relative to the longitudinal axis, wherein the other one of the second gripper and the counter second gripper is a recess or cut-out.

19. The package assembly as claimed in claim 17, wherein one of the first gripper and the counter first gripper is a hook or a protrusion radially extending relative to the longitudinal axis, where the other one of the first gripper and the counter gripper is a recess or cut-out.

\* \* \* \* \*